United States Patent [19]
Moo-Young et al.

[11] Patent Number: 5,733,565
[45] Date of Patent: Mar. 31, 1998

[54] MALE CONTRACEPTIVE IMPLANT

[75] Inventors: Alfred J. Moo-Young, Hastings-on-Hudson; Saleh I. Saleh, Queens, both of N.Y.

[73] Assignee: The Population Council, Center for Biomedical Research, New York, N.Y.

[21] Appl. No.: 606,063

[22] Filed: Feb. 23, 1996

[51] Int. Cl.⁶ .............................. A61F 2/02; A61K 47/32
[52] U.S. Cl. .......................................... 424/424; 514/772.3
[58] Field of Search ................................... 424/423, 424; 514/772.3

[56] References Cited

U.S. PATENT DOCUMENTS

| | | |
|---|---|---|
| 4,957,119 | 9/1990 | de Nijs . |
| 5,035,891 | 7/1991 | Runkel et al. ........................ 424/423 |
| 5,266,325 | 11/1993 | Kuzma et al. . |
| 5,292,515 | 3/1994 | Moro et al. . |

OTHER PUBLICATIONS

"Chemical Abstracts Search," Aug. 24, 1995, 65 pages.
"Contraception With Long–Acting Subdermal Implants," The International Committee For Contraception Research Of The Population Council, Mar. 20, 1985, 351–359.
"Clinical Trial With 3–Keto–Desogestrel Subdermal Implants," Center For Biomedical Research, The Population Council, Oct. 1991, vol. 44, No. 4, 393–408.
"Contraception With Subdermal Implants Releasing The Progestin ST–1435: A Dose–Finding Study," Jan. 1992, vol. 45, No. 1, 49–55.

"7α–Methyl–Nortestosterone (MENT): The Optimal Androgen For Male Contraception," Sundaran et al., *Recent Advances in Female Reproductive Health Care*, 199–205.

"Long–Term Contraception With A Single Implant Of The Progestin ST–1435," Coutinho et al., *Fertility& Sterility*, vol. 36, No. 6, Dec. 1981, 737–740.

"ST–1435: Development of An Implant," Odlind et al., 441–449.

*Contraception*, Mar. 1982, vol. 25, No. 3, 300–306.

"A Contraceptive Subdermal Implant Releasing Progestin ST–1435: Ovarian Function, Bleeding Patterns and Side Effects," Laurikka–Routti et al., *Fertility & Sterility*, vol. 58, No. 6, Dec. 1992, 1142–1147.

"Endometrial Effects Of Transdermal Estradiol & Progestin ST–1435 In Post Menopausal Women," Suhonen et al., *Fertility &Sterility*, vol. 57, No. 6, Jun. 1992, 1211–1215.

*Primary Examiner*—Carlos Azpuru
*Attorney, Agent, or Firm*—Lerner, David, Littenberg, Krumholz & Mentlik

[57] ABSTRACT

The present invention relates to implantable male contraceptive devices. An ethylene vinyl acetate copolymer based implant is described for delivery of an androgen and a system including an ethylene vinyl acetate copolymer based implant as well as a second implant are described for the administration of both androgen and a sterilitant. These implants may be used to provide contraception for men, as well as, for hormone therapy, treatment of enlarged prostate and other aliments.

36 Claims, 5 Drawing Sheets

MALE CONTRACEPTIVE IMPLANT

FIELD OF THE INVENTION

The present invention relates to the field of male contraception as well as the treatment of benign prostrate hypertrophy, and other conditions which can be treated by androgen or hormone therapy and to methods and apparatus regarding same.

BACKGROUND OF THE INVENTION

Contraception is a difficult subject under any circumstance. It is fraught with cultural and social stigma, religious implications and, most certainly, significant health concerns. This situation is only exacerbated when the subject focuses on male contraception.

Despite the availability of suitable contraceptive devices, historically, society has looked to women to be responsible for contraceptive decisions and their consequences. Although health concerns over sexually transmitted diseases has made men more aware of the need to develop safe and responsible sexual habits, women still often bear the brunt of contraceptive choice.

There are many plausible explanations for this social phenomenon. One explanation stems from the different choices available to men and women who wish to avoid becoming parents. Women have a number of choices from temporary mechanical devices such as sponges and diaphragms to temporary chemical devices such as spermacides. Women also have at their disposal more permanent options such as physical devices like IUDs and cervical caps as well as more permanent chemical treatments such as birth control pills and subcutaneous implants. However, to date, men have only had one principal and convenient means of contraception, namely condoms. Condom use, however is not favored by many men because of the reduced sexual sensitivity, the interruption in sexual spontaneity, and the significant possibility of pregnancy caused by breakage or misuse. Condoms can also be inconvenient and uncomfortable just at the time when convenience and comfort are at a premium.

If more convenient methods of birth control were available to men, particularly long term methods which required no preparative activity immediately prior to a sexual act, such methods could significantly increase the likelihood that men would take more responsibility for contraception.

One of the more vogue concepts in contraception is the subcutaneous implant. Under this contraceptive strategy, an implantable device is placed just beneath the skin from which contraceptive chemicals can diffuse into the body.

Any number of devices have been proposed for the subcutaneous delivery of drugs in general. Many of these devices may be used for the subcutaneous delivery of contraceptives. Indeed, a number of devices have been proposed and used for subcutaneous contraceptive systems for women including the much publicized NORPLANT® and NORPLANT II® systems which use a silicone elastomer, such as, for example, SILASTIC®, siloxane-containing material available from Dow Corning for the implant. See U.S. Pat. Nos. 4,957,119, and 5,088,505 as well as Haukkamaa, Laurikka-Routti, Heikinheimo, Moo-Young, "Contraception With Subdermal Implants Releasing The Progestin ST-1435: A Dose-Finding Study", CONTRACEPTION, "1992", 45, 1, pgs. 49–55; Odlind, Lithell, Kurenmaki, Lahteenmaki, Toivonen, Luukkainen, Johansson, "ST-1435: Development of an Implant", "1984"; Pages 441–449, Coutinho, Silva, Carreira, Sivin, "Long-Term Contraception With A Single Implant Of The Progestin ST-1435*", Fertility and Sterility", "1981", 36, 6, Pages 737–740; Lahteenmaki, Weiner, Lahteenmaki, Johansson, Luukkainen, "Pituitary And Ovarian Function During Contraception With One Subcutaneous Implant Releasing A Progestin, ST-1435", CONTRACEPTION, "1982", 25, 3, pgs. 299–306; Robertson, Diaz, Alvarez-Sanchez, Holma, Mishell, Countinho, Brache, Croxatto, Faundes, Lacarra, Pavez, Roy, de Silva, Sivin, Stern, "The International Committee for Contraception Research (ICCR) of the Population Council", CONTRACEPTION, "1985", 31, 4, Pages 351–359; Diaz, Pavez, Moo-Young, Bardin, Croxatto, "Clinical Trial With 3-Keto-Desogestrel Subderma Implants", CONTRACEPTION, "1991", 44, 4, Pages 393–408; Laurikka-Routti, Haukkamaa, A Contraceptive Subdermal Implant Releasing The Progestin ST-1435: Ovarian Function, Bleeding Patterns, And Side Effects", Fertility and Sterility, "1992", 58, 6, Pgs. 1142–1147.

There have also been proposals for the construction of subcutaneous implantable male contraceptives. See Sundaram et al., "7 Alpha-Methyl-Nortestosterone(MENT): The Optimal Androgen For Male Contraception", Annals of Medicine, (1993), 25, 199–205. However, as those very same proposals demonstrate, the challenges facing long term male contraception are significant. As that paper cautions, one cannot merely administer compounds which block gonadotrophin secretion and sperm production because such compounds will also generally decrease testosterone production. Therefore, androgens must be an essential part of any overall contraceptive strategy. Commonly, androgen supplementation is achieved by the use of testosterone administration. However, this generally requires frequent and large doses which are costly and inconvenient. Peaks of testosterone concentration may also result which could stimulate spermatogenesis. See Annals Of Medicine 25: 199–205, 1993.

Sundaram et al., investigated the possibility of delivering 7α-Methyl-19-Nortestosterone (MENT) and its acetate derivative (MENT Ac) in place of testosterone in an implantable contraceptive system. As the results of that study indicated, MENT can be an effective part of a two component implantable system for male contraception with the other component being an implant that will release LHRH or its analogs. However, the system employed in the Sundaram et al. paper is clearly impractical for long term use in humans. For example, experiments were designed where an LHRH agonist was delivered via a subcutaneously implanted osmotic pump. The pump had to be replaced at monthly intervals. This would not be practical for human male contraception. Moreover, silicone elastomer implants which are commonly used in female contraceptive implants, e.g., the NORPLANT® system, could not be used for the long-term delivery of MENT Ac, because the release rate of the steroid was much too rapid.

If an implant could be designed to provide a consistent, long term delivery of androgen and if that implant could be combined with a suitable system for delivery of LHRH, its analogs, or functionally related compounds, the resulting system could be highly successful, if not indeed the method of choice, among men making contraceptive decisions. Such devices could also have indications for treating hypogonadism, prostatic hyperplasia and muscle wasting.

SUMMARY OF THE INVENTION

One aspect of the present invention is the provision of an implantable device capable of delivering androgen to a patient in need of androgen therapy. Such devices may be useful in combination with sterilitants in providing male contraceptive systems. The device can also be used in any other therapeutic protocol which involves the administration of androgen such as, for example hypogonadism, prostatic hyperplasia, and muscle wasting. The implant is intended for subcutaneous or local administration and includes androgen in an amount which is sufficient to provide to a patient, the required daily dose of a pharmaceutically effective amount of the androgen over a period of at least seven days. The androgen is dispersed in a core of ethylene vinyl acetate copolymer having a sufficient molecular weight so as to result in a melt index which is greater than 10 grams/10 minutes, and a vinyl acetate content of at least about 20% by weight. The device also includes a membrane or tubing that encases the rod containing the androgen. The thickness of this membrane or tubing is at least 50 micrometers. The membrane is made of ethylene vinyl acetate copolymer having a molecular weight which results in a melt index which is less than 10 grams/10 minutes and a vinyl acetate content of less than 20% by weight. In a particularly preferred aspect of the invention, the androgen is MENT Ac.

This first implant may be used alone, or in combination with other therapies and devices. For example, the first androgen releasing implant may be used in combination with a vaccine such as luteinizing hormone-releasing hormone (LHRH) to provide male contraception or to treat benign prostatic hypertrophy (BPH).

Also provided in accordance with the present invention is a dual implant system useful for providing long-term male contraception as well as in the treatment of other medical conditions. For example, the system may also be used to treat BPH. In accordance with this aspect of the present invention there is provided an implantable system which includes a first implant intended for subcutaneous or local administration of an androgen. The first implant has an androgen provided in an amount which is sufficient to provide for the required daily dose of a pharmaceutically effective amount of the androgen over a period of at least seven days, disposed in a core formed of a first ethylene vinyl acetate copolymer. The core is covered by a membrane. The membrane is formed of a second ethylene vinyl acetate copolymer. A second implant intended for subcutaneous or local administration of a sterilitant is also provided. The second implant contains a sterilitant in an amount which is sufficient to provide for the required daily dose of a pharmaceutically effective amount of the sterilitant. The first implant and the second implant have a complementary size and shape and are designed such that each releases a pharmaceutically complementary amount of the androgen and the sterilitant, respectively, so as to provide treatment to a patient in need thereof.

In a particularly preferred embodiment in accordance with the present invention, the second implant used is a biocompatible, non-biodegradable, water-swellable, water-insoluble, hydrophilic cartridge of a copolymer AB having from about 25 to about 70 weight percent of 2-hydroxy ethyl methacrylate (monomer A) units and from about 75 to about 30 weight percent of monomer B units and possessing a predetermined equilibrium water content (EWC) value in the range of from about 25 to about 75 weight percent. A sealant for closure of an open end of the cartridge comprising a plug of biocompatible, non-biodegradable, water-swellable, water-insoluble, hydrophilic polymer having an EWC value greater than that of the cartridge is also provided. The sterilitant is contained in a reservoir disposed within the cartridge.

Embodiments of the present invention also include methods of using a first, androgen containing, implant in a contraceptive system, methods of using the first implant for the treatment of other medical conditions and the use of both first and second implants for the treatment of various medical conditions as well as for providing contraception. Also provided in accordance with the present invention is a kit containing at least one first and at least one second implant, specifically designed to be used in conjunction with one another and to be implanted subcutaneously in a patient.

DETAILED DESCRIPTION OF THE PREFERRED EMBODIMENT

Figure 1:
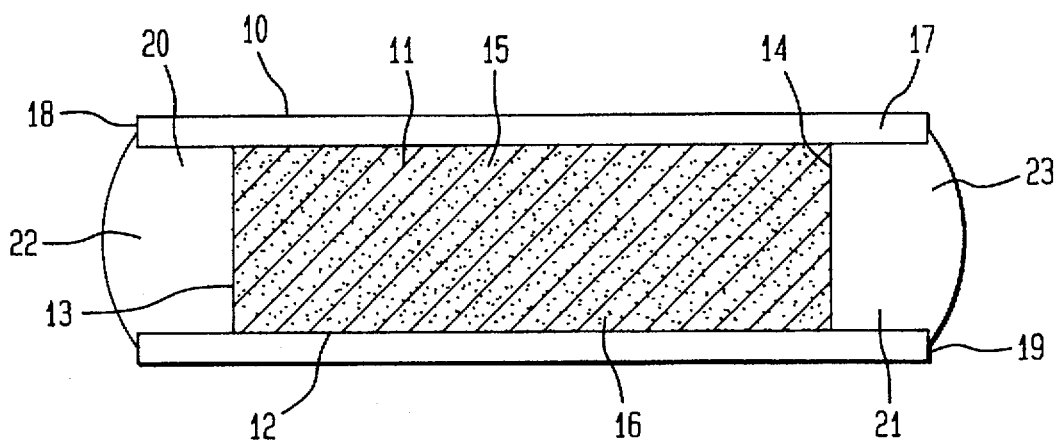
FIG. 1 is a cross sectional view of the first implant of the present invention.

Designers of contraceptive implants for women have a considerable degree of flexibility as most female contraceptive agents can be successfully administered through a wide variety of delivery devices. For that reason, the inventors anticipated the same degree of design flexibility when producing male contraceptive implants. However, the inventors unexpectedly and surprisingly found that such was not the case. In fact, subcutaneous implants for male contraception proved to be quite unpredictable. As explained in Sundaram et al., "7 Alpha-Methel-Nortestosterone(MENT): The Optimal Androgen For Male Contraception", *Annals of Medicine*, (1993), 25, 199–205, discussed earlier, traditional silicone elastomer implants, used in female contraceptive systems such as NORPLANT®, but administering MENT Ac, needed to be replaced at three week intervals during tests because of rapid loss of androgen. As is aptly demonstrated by FIG. 2, silicone elastomer delivery vehicles, which are prevalent in contraceptive implants for women, are ineffective and impractical for the delivery of androgen because of the rapid rate of androgen release. To further complicate matters, the inventors also made implants out of ethylene vinyl acetate copolymers using MENT as described herein and while these implants worked, the release of the androgen was considerably slower than the same device using androgen in it acylated form. As shown in FIG. 3, When MENT and MENT Ac were both formulated in identical EVA implants, MENT released at a rate of less than 20 µg/implant/day while MENT Ac was released at a rate which was at least about 300 µg higher.

It was subsequently determined that a particular combination of ethylene vinyl acetate ("EVA") copolymer formulations were advantageous for the construction of implant delivery devices for androgen where other combinations were not. Moreover, it was determined that a particular combination of MENT Ac and certain EVA copolymer delivery vehicles could provide particularly effective, long term release of androgen so as to be useful as part of a male contraceptive strategy and/or in the treatment of certain other medical conditions. Most preferably, the androgen releasing implants of the present invention could be designed to coordinate the delivery of androgen with the delivery of other agents so as to provide an effective, long term, implantable male contraceptive system.

The term "androgen" as used in accordance with the present invention encompasses male sex hormones. The androgenic hormones are steroids which are produced in the body by the testis and the cortex of the adrenal gland or synthesized in the laboratory. These include testosterone and its esters such as the buciclate, cypionate, propionate, phenylpropionate, cyclopentylpropionate, isocarporate, enanthate and decanoate. Synthetic androgens such as MENT and its esters such as MENT Ac are also encompassed by the term. The first implant may also be used to deliver functionally related compounds such as anabolic agents. These agents generally exhibit strong anabolic potency and relatively weaker androgenic activity. These compounds include methandriol, oxymetholone, methandienone, oxymesterone, nondrolone phenylpropionate and norethandrolone. The esters of all of the above compounds are preferred.

The first, androgen-releasing, implant of the invention includes a core material of EVA copolymer having such a molecular weight that the melt index is greater than 10 grams per 10 minutes, and a vinyl acetate content of 20% by weight or more. This core material functions as a matrix or reservoir for androgen. The membrane which has a layer thickness of 50–250 μm and encases the core also consists of a EVA copolymer. However, this second EVA copolymer has a molecular weight such that the melt index is less than 10 grams per 10 minutes, and a vinyl acetate content of less than 20% by weight. Preferably, the resulting implant is cylindrical with a maximum external diameter of about 3.0 mm and a maximum length which is about 5.0 cm.

The core material can be charged with up to about 75 percent by weight of the androgen without seriously affecting the utility of the EVA core material made of the first EVA copolymer. The degree of charging of between about 50–65% by weight is preferred.

In a particularly preferred embodiment of the present invention, the core material or first EVA copolymer used in the present invention is an EVA copolymer with a melt index greater than 10 gram/10 min. and preferably between 25 and 30 grams/10 min. The vinyl acetate content is greater than 20% by weight and most preferably between 25%–40% by weight.

Very suitable EVA polymers which can be used as core material are, for example, Evatane® with the designations 28–150, 28–399, and 28–400, supplied by ICI and 28.420, 28.25 and 33.25 supplied by Atochem, and Elvax® with designations 310, 250, 230, 220 and 210, supplied by Du Pont de Nemours. Polyethylene-co-vinyl acetate, 25 wt % vinyl acetate supplied by Aldrich Chemical Co. Inc. could also be used, for example.

The membrane polymer is also made of an EVA polymer. However, this second EVA copolymer has a higher molecular weight than the first EVA copolymer of the core. The melt index of this membrane material is less than 10 g/10 min., and preferably less than or equal to 8 g/10 min. More preferably, the melt index is less than about 5 grams/10 min. and most preferably about 4 grams/10 min. The vinyl acetate content is less than 20% by weight. The second EVA copolymer could have, for example, a composition of about 9–12% VA polymer content.

Suitable EVA polymers which can be used as a membrane are, for example, Evatane® with the designations 501/502 (melt index 2, vinyl acetate content 7.55%), 554/555 4, 12.5%), 540(10, 18%) and particularly 571 (8, 15%), Elvax® with the designations 450, 460, 470, 550, 560, 650, 660, 670, 750, 760 and 770, and Evatane® 1080 VN 5 and in particular 1040 VN 4 supplied by Atochem. The release characteristics or release rate of the androgen through the membrane are determined, to a large extent, by the vinyl acetate content of the second EVA copolymer.

The first subdermally implantable androgen delivery device according to the present invention can be easily fabricated in accordance with standard techniques. Generally, once the androgen is mixed with the matrix material to achieve a substantially uniform dispersion, it is then processed to the desired shape by molding, casting, extrusion, or other appropriate process. The outer layer can be applied to the central core in a variety of ways such as by mechanical stretching, swelling or dipping. See, for example, U.S. Pat. Nos. 3,832,252, 3,854480 and 4,957,119, the texts of which are hereby incorporated by reference.

In a preferred method, EVA pellets are dissolved in a solvent such as, for example, methylene chloride. The resulting solution is agitated and the androgen is added thereto. The solvent is then evaporated under vacuum. The obtained solid dispersion is filled into a metallic syringe or an extruder and heated. Then, the material is extruded. The obtained rod is then cut down to the desired size. The dimensions of the implant are also determined, at least in part, based on the implantation method, length of useful life, androgen volume and the like. EVA tubing is next cut into pieces which are slightly longer than the cut pieces of rod. The tubing pieces are then soaked in solvent for a brief time (on the order of minutes). The rod is introduced into the lumen of one of the pieces of soaked EVA tubing leaving about 0.5 cm empty from both ends. The tubing preferably has an outside diameter of 2.39–2.55 mm and an inside diameter or lumen of 2.13–2.36 mm. The filled tubing is then dried. The two ends of tubing are sealed by filling with melted EVA. The sealed tubing is then heated briefly to enhance the sealing and the adherence between the inside rod and the outside tubing and the end seals. This will also ensure evaporation of any traces of methylene chloride. The two ends of the filled tubing are trimmed leaving about 2.5 mm as a sealing tip. The ends of the device can also be sealed in a variety of other ways in accordance with art-recognized techniques. For example, the overlying ends of the outer layer can be singed, crimped, pinched or sealed with for example, radio-frequency. The obtained implants can be suitably sterilized using, for example ethylene oxide, and packaged. The first implant of the invention may also be produced by means of a so-called co-axial extrusion process.

The first implant will preferably have a maximal external diameter of about 3 mm and more preferably between about 2.4 and about 2.7 mm. The length of the implant will preferably be less than about 5 cm and more preferably between about 4.4 and 4.6 cm.

FIG. 1 illustrates a longitudinal cross-sectional view of a partially assembled first implant 10 which contains a central core 11 extending in an axial direction and having an outer surface 12 and opposing ends 13 and 14. The central core 11 is a matrix of a pharmaceutically effective amount of subdermally administrable androgen 15 substantially uniformly dispersed in a first EVA copolymeric base 16. Membrane 17 overlies the core 11. Membrane 17 has opposed ends 18 and 19 which extend axially beyond opposing ends 13 and 14, respectively, of central core 11 to define cavities 20 and 21, respectively.

Upon complete assembly of the device cavities 20 and 21 are substantially filled with ethylene vinyl acetate copolymer (EVA) with a 25% vinyl acetate content forming seals 22 and 23. Seals 22 and 23 disposed, in cavities 20 and 21, respectively, cooperate with overlying ends 18 and 19, respectively of membrane 17 to completely encapsulate the central core 11. The sealant minimizes the diffusion of the drug in the axial direction, i.e., from the ends of the device. The potential for undesired axial diffusion of the drug increases as the length of the implant decreases, e.g., to about 3.0 cm and less. The seals 22 and 23 also serve to more securely hold the device together, e.g., maintain the structural integrity of the device, and prevent the infiltration of the biological tissue into the otherwise open ends of the device.

Figure 6:
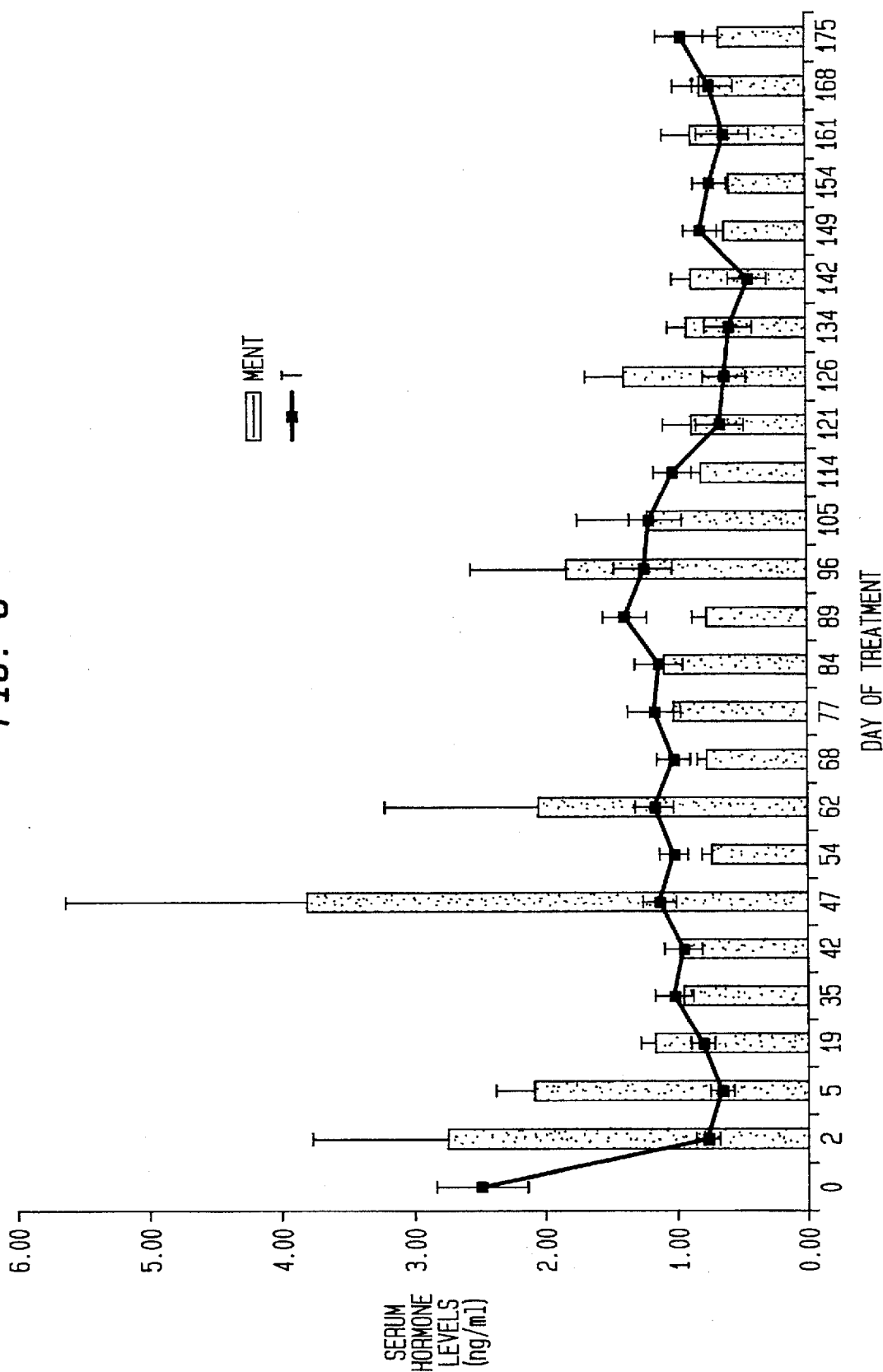
FIG. 6 is a graph showing serum levels of MENT Ac (measured as MENT), and testosterone ("T").

The first implant of the invention should contain a quantity of androgen which is sufficient to provide for the required daily dose of a pharmaceutically effective amount of said androgen over a period of at least seven days. The implant should also be designed to insure as near a zero-order release profile of the androgen over that same period of time as possible. A pseudo-zero order release profile (following there initial burst) is illustrated in FIG. 6. A "pharmaceutically effective" amount of androgen is that amount sufficient to support the sexual function (used in combination with male antifertility implant, vaccine or other drug leading to suppression of testosterone) for a predetermined time period, e.g., the useful life of the implant. The weight ratio of the polymeric base material to the androgenic agent in the central core will generally range from 1:1 to 2.5:7.5. The first implant of the present invention should contain a sufficient quantity of the androgen to provide a substantially constant release of a daily dosage of from between about 100 and about 1,000 micrograms and, more preferably, between about 200 to about 500 micrograms of androgen over the useful life of the implant.

While the first implant should be able to deliver androgen for a period of at least seven (7) days, much longer periods are contemplated. It is preferred that the first implant be capable of supplying androgen for about 100 to 180 days or even longer. Depending upon the androgen, the actual composition of the first EVA copolymer, and the size of the first insert, androgen administration could last for as long as one year, if not longer. In general, the core will contain from about 10 mg to about 145 mg of the androgenic agent.

The first implant of the present invention can be prepared in a variety of sizes and shapes to accommodate such factors as the specific implantation site and the desired release rate of the drug. In a preferred embodiment wherein the androgen is MENT Ac, the device is substantially cylindrical in shape having a preferred overall length of about 4.4 cm to about 4.6 cm, and a preferred overall diameter of about 2.4 mm to 2.7 mm. In such a case, the central core is rod-shaped, and has a preferred length of about 3.8 cm to about 4.2 cm, and a preferred diameter of from about 2 mm to about 2.4 mm. This will produce an implant with a useful life of at least about 100 days and preferably about 180 days, or longer, for a normal male. These dimensions can be modified depending upon such factors as the location of implantation, the subject, the condition to be treated, the androgen, the desired release rate of the androgen, the number of first implants to be used at one time and the other factors previously discussed.

The first implant may be used alone for certain types of therapeutic use. These include: Hypogonadism, Cryptochidism, Male Climacteric, Impotence, and as an anabolic agent. However, in a preferred aspect of the present invention, the first implant is used in coordination with a second implant intended for the subcutaneous or local administration of a sterilitant.

Figure 7:
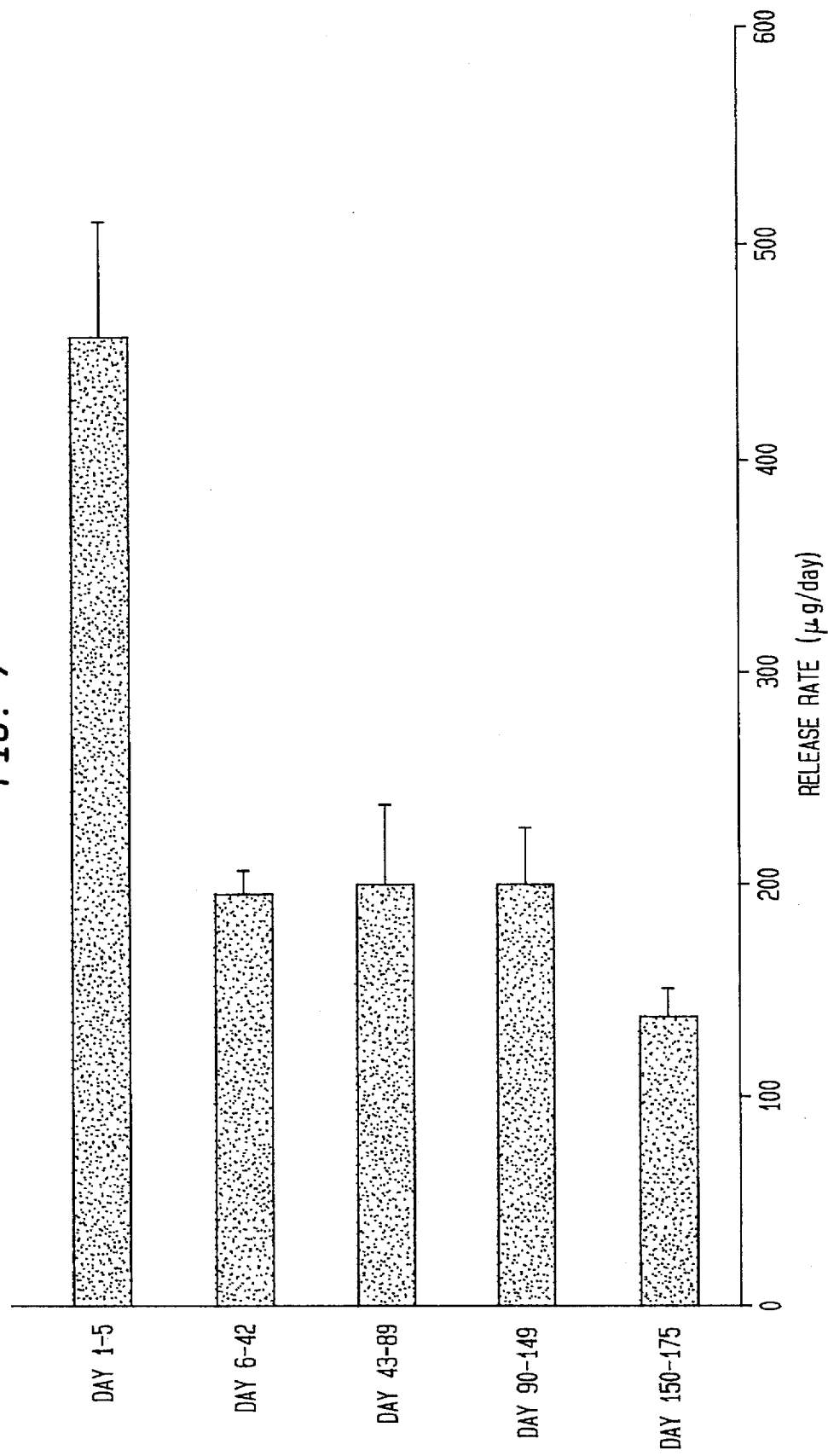
FIG. 7 illustrates the in vivo release rate of MENT Ac (measured as MENT) (micrograms/day) over the day ranges shown based on metabolic clearance rate and serum levels of the steroid.

First implants prepared in accordance with the present invention and, in particular, Example 1, were implanted, subcutaneously into male cyanmologous monkeys in the region of their abdomen. As shown in FIG. 6, blood was drawn from the monkeys on the days indicated along the x axis and the serum hormone levels, in nanograms per milliliter, were determined. The first implants used delivered MENT Ac. However, MENT Ac is metabolized to MENT within the body and it was MENT concentration in blood which was determined. For comparison purposes, blood levels of testosterone ("T") were also measured. Based on these blood levels, and the metabolic clearance rate ("MCR") of MENT Ac (187.6 L/day) obtained from previous experiments, the in vivo release rate of the MENT Ac implants of the present invention was calculated using the following formula: RR=MCR×Css where "RR" equals the release rate and "Css" equals the serum concentration at steady state (values determined from FIG. 6). The results are tabulated in Table 1 below and are illustrated graphically in FIG. 7.

TABLE 1

| Date Range | Css (μg/L) | Rel. Rate (μg/day) |
| --- | --- | --- |
| Day 1-5 | 2.44 ± 0.30 | 457 ± 55.3 |
| Day 6-42 | 1.03 ± 0.07 | 194 ± 13.0 |
| Day 43-89 | 1.06 ± 0.21 | 199 ± 38.6 |
| Day 90-149 | 1.06 ± 0.14 | 199 ± 26.2 |
| Day 150-175 | 0.76 ± 0.07 | 136 ± 13.3 |

The data indicates that after an initial burst in the first five days, a generally zero order or pseudo zero order release rate was observed, at least through day 150. Thereafter, towards the end of the useful life of the implant, some diminished release rate was observed.

Sterilitants are drugs which kill sperm, interrupt sperm production, suppresses sperm production, or render sperm unable to fertilize an egg. The effects of these sterilitants are generally reversible. That is, once they are removed, sperm production and/or viability return. A preferred subclass of sterilitants used in accordance with the present invention is LHRH (luteinizing hormone-releasing hormone)peptides as well their analogs and functionally similar compounds. These compounds are active polypeptides which act on the anterior pituitary gland to effect release of hormones that affect the activity of reproductive organs. Naturally occurring LHRH peptide is produced in the hypothalamic region of the brain and controls the reproductive cycle of mammals by acting to effect the release of luteinizing hormone and follicular stimulating hormone which in turn acts on the gonads to stimulate the synthesis of steroid hormones and to stimulate gamete maturation. LHRH can be used for hypogonadal conditions and impotence and for stimulating spermatogenesis, and androgen production in the male. Large doses of highly potent and long lasting analogs of LHRH have the opposite effect; suppressing spermatogenesis in the male. Thus, this material can act as a chemical sterilitant. See U.S. Pat. Nos. 4,234,571, 5,292,515 and 5,266,325. Other LHRH analogs are known which provide, at lower dose levels, chemical sterilitant activity in males as well.

In accordance with the present invention these sterilitant compounds may be administered through a second implant which differs significantly in its structure and composition when compared to the first androgen delivering implant. One group of delivery implants useful as the second implant in accordance with the present invention is a hydrogel implant. Hydrogel based delivery systems for LHRH and its analogs are known and are described in U.S. Pat. Nos. 5,266,325 and 5,292,515, the texts and drawings of which are hereby incorporated by reference.

In one embodiment, the second implant is formed from a homogeneous hydrophilic copolymer having a predetermined equilibrium water content or "EWC" value. This material can be produced by the addition polymerization of a mixture containing ethylenically unsaturated hydrophilic monomer A and an ethylenically unsaturated hydrophilic monomer B copolymerizable therewith. The copolymer is useful as a hydrogel membrane in the diffusion therethrough of a selected active compound, (sterilitant), in an aqueous, or nonaqueous medium, at a predetermined rate.

The second implant is preferably a uniform, homogeneous, water-insoluble, water-swellable copolymeric, cylindrically-shaped article with a concentric core having a predetermined equilibrium water content value. The implant is formed by the addition polymerization of a mixture containing ethylenically unsaturated hydrophilic monomer A and ethylenically unsaturated monomer B copolymerizable therewith. This can provide an implantable device which is useful for the sustained release of an active agent therefrom to a patient. This embodiment involves: a. forming a polymerizable liquid mixture containing monomer A and monomer B in amounts sufficient to yield a homogeneous copolymer AB having a predetermined equilibrium water content value; b. introducing into the open end of a polymerization column a predetermined amount of said polymerizable liquid mixture; c. rotating said polymerization column about its longitudinal axis maintained substantially parallel to the ground at a speed sufficient to cause radially outward displacement of said polymerizable liquid mixture to assume a predetermined hollow cylindrical liquid configuration within said column; d. maintaining the polymerization column under polymerization conditions to convert said polymerizable mixture of predetermined liquid configuration into a predetermined solid hollow cylindrical configuration; and e. recovering a copolymeric cylindrically-shaped article having the predetermined equilibrium water content value and further characterized by a cylindrical core or reservoir and smooth internal and external cylindrical surfaces of substantially uniform thickness between said surfaces. In a preferred embodiment, a homogenous hydrophilic copolymer of 2-hydroxyethyl methacrylate ("HEM") and hydroxypropyl methacrylate ("HPFLA") are produced and used.

In one embodiment, the second implant is a uniform, cylindrically-shaped copolymeric cartridge characterized by a predetermined EWC value, produced with a substantial uniformity of thickness between its outer and inner cylindrical surfaces using a pore-forming agent uniformly or homogeneously distributed throughout the cartridge. In this aspect of the invention, a uniform or homogeneous polymerizable liquid mixture of monomer A, monomer B, and a pore-forming agent, is prepared using amounts sufficient to result in a homogeneous copolymer having the targeted EWC value.

Another embodiment of the second implant involves the preparation of a delivery device for the delayed/sustained release of an active agent therefrom e.g., a drug, which comprises: a. introducing active agent and, optionally, a pharmaceutically acceptable carrier, into the core (reservoir) of the aforesaid cylindrically shaped copolymeric body in an amount sufficient for extended sustained release of said active agent into a delivery environment; b. further introducing polymerizable liquid material into the said core in an amount sufficient to cover the active agent or to substantially or completely fill the core to the top of the cylindrical body, said polymerizable liquid material in its polymerized state having an equilibrium water content value which exceeds the equilibrium water content value of the cylindrical body; and c. polymerizing said polymerizable material to effectively seal the core opening with a plug (layer) of water-swellable, water-insoluble polymer.

The delayed/sustained release implant comprises a hydrophilic copolymeric cartridge of xerogel or hydrogel (collectively referred to as a hydrogel herein). The implant also includes a hydrophilic sealing means to seal the open end of the cartridge thereby defining an enclosed core, a sterilitant and optionally, a pharmaceutically acceptable carrier, contained in the core in an amount sufficient to be continually released over an extended period of time. The cartridge is characterized by water-swellability, water-insolubility, smooth, unscored outer and inner cylindrical surfaces, and a predetermined EWC value. The hydrophilic sealing means exhibits water-swellability, water-insolubility, and an equilibrium water content value which exceeds that of the cartridge.

Figure 4:
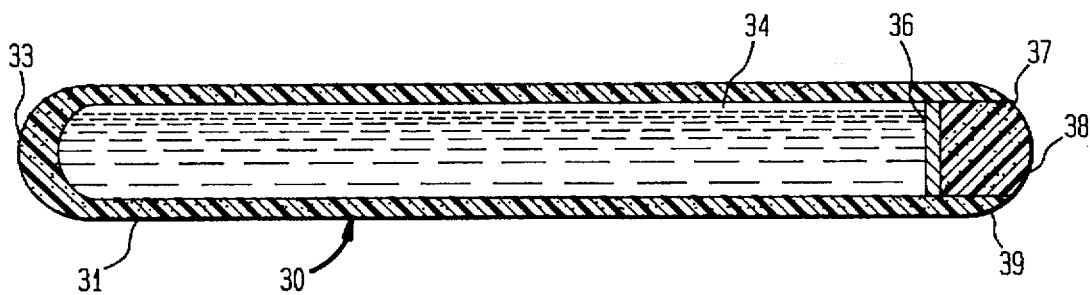
FIG. 4 is a cross sectional view of the second implant of the present invention.

FIG. 4 illustrates one form of the second implant 30 of the invention. Cartridge 31 is shown with an oval-like base 33 (after trimming and polishing) packed with drug such as LHRH analogs 34 in its core. The external and internal cylindrical services of cartridge 30 are smooth and unscored. Teflon covered 36 separates drug 34 from hydrophilic plug 37, formed in situ from liquid material and polymerized to a solid hydrophilic plug 37. The equilibrium water content of plug 37 and thus its swellability are greater than the EWC of cartridge 31. Therefore, a hermeticial seal will be formed upon hydration. The outer surface 38 of plug 37 including a portion of the contiguous cartridge wall 39 has been oval shaped by trimming and polishing.

The amount of LHRH or its analogs will depend on many factors. However, principally, the amount will depend upon the rate and extent of release, the useful life of the implant, the physical size and needs of the patient, the type of treatment for which the implants are prescribed and, of course, the need to complement the administration of androgen from the first implant previously described. Treatment of infertility with synthetic LHRH peptides requires a low level of drug, while reduction of fertility and related effects requires a large dose relative to the activity of naturally occurring LHRH. For LHRH agonist fertility control, it is desired to release the drug at such a rate that the subject will receive between 0.05 and about 100 micrograms per kilogram of body weight per day, preferably between 0.1 and 5.0 micrograms per kilogram body per day.

The result is a second implant for sustained release of an active agent such as this sterilitant therefrom which includes a biocompatible, non-biodegradable, water-swellable, water-insoluble, hydrophilic cartridge of an AB copolymer, a sealant for closure of the open end of the cartridge which includes a plug of biocompatible non-biodegradable, water-swellable, water-insoluble hydrophilic polymer having an equilibrium water content value greater than that of the cartridge per se. The sterilitant, either alone or in combination with other carriers, diluents or active ingredients, is contained in the reservoir of the cartridge in an amount sufficient to provide the predetermined sustained release thereof over the useful life of the implant. Most preferably, the copolymer AB consists of from about 25 to 70 weight percent of 2-hydroxy ethyl methacrylate (monomer A) units and from 75 to 30 weight percent of monomer B units. The B units possess predetermined EWC value in the range of 25 to about 75 weight percent. The monomer B can be hydroxy propyl methacrylate units.

In an embodiment, the two implants may be provided to the attending physician in a single kit, ready for use. The kit would include two implants, one for the delivery of an androgen and one for delivering a sterilitant. Preferably, at least one of the implants will already be loaded into one a device capable of administering the implant directly to the patient. For example, each could be separately loaded into a syringe or trocar for subcutaneous administration. Most preferably, the second implant will be hydrated in saline and stored in hypertonic saline.

The kit may also include gauze, trocars, scalpels and the like, all in a sterilized container. The first implant can be sterilized by use of ethylene oxide. However, the second implant is preferably sterilized by steam.

However, it will often be beneficial to administer the first and the second implants at different times. For example, the second implant would be implanted first, with the first androgen containing implant being implanted when the testosterone levels become significantly depressed (about castration levels). This may occur weeks later. Of course, both implants may still have been provided in a single kit. However, individual kits, designed to be mixed and matched may be provided for each implant.

Of course, the present invention is not limited to a system which uses a hydrogel implant as described herein for the second implant. Any implant which is capable of delivering one or more sterilitants in a manner which is complementary to the first implant previously described may be used.

In vitro diffusion of either androgen, from the first implant or the diffusion of the sterilitant from the second implant is an indication of the diffusion characteristics of the implants in vivo. In vitro diffusion of the drug from either the first or the second implant may be determined, for example by the methods disclosed in Chien et al., *J. Pharm. Sci.*, 63,365 (1974), or by the methods described in U.S. Pat. No. 3,710,795. In vivo diffusion can be measured by, for example, the methods described in Sundaram et al., "7 Alpha-Methel-Nortestosterone (MENT): The Optimal Androgen For Male Contraception", *Annals of Medicine*, (1993), 25, 199–205.

The devices of the present invention can be implanted into a subject in accordance with standard procedures. By the term "subject" it is meant mammals, e.g., humans, valuable domestic household, sport or farm animals, the laboratory animals. In the case of these implants, for example, this procedure is advantageously performed with a trocar and the device is preferably implanted beneath the skin of the upper arm of the patient. See Shoupe et al., Am. J. Obstet. Gynecol., 160: 1286–92 (1989), and Tikkanen et al., J. Reprod. Med., 31: 898–905 (1986).

EXAMPLES

The invention will be further described by reference to the following detailed examples. These examples are provided for purposes of illustration only, and are not intended to be limiting unless otherwise specified.

Example 1

Preparation of a First Eva Implant(MENT Ac)

A. Extrusion of core rods containing 60% w/w MENT Ac.

1 g of EVA pellets, 25% VA content, (Aldrich Chemical Company Inc., GRAFTSMEN IN CHEMISTRY MILWAUKEE WIS 53233 USA) was soaked in 12 ml of methylene chloride (Fisher Scientific). The obtained solution was vortexed before and after the addition of 1.5 g of MENT Ac. Methylene chloride was evaporated under vacuum (at room temperature) for 2 hours. The obtained solid dispersion was filled into a metallic syringe and heated to 110° C. for 5 minutes and then extruded through the 0.1 inch nozzle of the metallic syringe. The obtained rod was cooled and cut down into 4 cm pieces.

B. Filling of the rods into the EVA tubing.

EVA tubing (9% VA content, about 2.55 mm in diameter) was cut into 5 cm pieces. The tubing has a wall thickness of from about 0.14 mm to about 0.17 mm. The 5 cm pieces were soaked in methylene chloride for about one minute.

Each of the 4 cm rods was introduced into the lumen of one of the 5 cm piece of the soaked EVA tubing leaving about 0.5 cm empty from both sides. The filled tubing was left overnight at room temperature to allow for the evaporation of the methylene chloride. The two ends of tubing were then sealed by filling with melted EVA (25% VA content).

The sealed implants were heated at 70° C. for 5 to 10 minutes to enhance the sealing and the adherence between the inner rod, the outside tubing and the end seals. This will also ensure evaporation of any traces of methylene chloride.

The two ends of the filled tubing were trimmed leaving about 2.5 mm as a sealing tip.

The obtained implants could be suitably sterilized and packaged.

C. Extrusion into a brass mold with lumens of the required diameter.

The same procedure as above except that the extrusion from the heated metallic syringe was affected into a brass mold with lumens with the appropriate diameter for example, 2.38 mm. The mold was preheated to facilitate the filling process, This procedure could be advantageous to ensure the uniformity of the diameter of the obtained core rods.

Encasement of the core rod by EVA tubing is described previously in B.

Example 2

In Vitro Release Profiles of Eva-MENT Ac Implants

As illustrated in FIG. 3, the implantable devices according to the present invention achieved substantially zero-order release of MENT Ac. Thus reliable, long-term therapeutic benefits such as maintaining secondary sexual function in conjunction with male contraception implants may be obtained.

Measurement of In Vitro Diffusion MENT Ac Implants

Glue each of implants produced above to the bottom of each individual glass vial (about 25 ml capacity) using Medical Adhesive. Quantitatively measure 20 ml of 1:750 ZEPHIRAN® solution, available to Winthrope Labs, a division of Sterling (Benzalkonium chloride solution supplied in a 17% aqueous solution) into each of the vials. Screw the cap to the vial and place it in a horizontal position in the appropriate rack in the water bath. Adjust the temperature to 37°±1° C. and shaking speed to 100±2 strokes per minute. Change solutions daily, and continue to incubate. Assay samples daily using UV spectrophotometer at the appropriate wave length (243 nm). ZEPHIRAN® solution is used as a reference standard.

Figure 5:
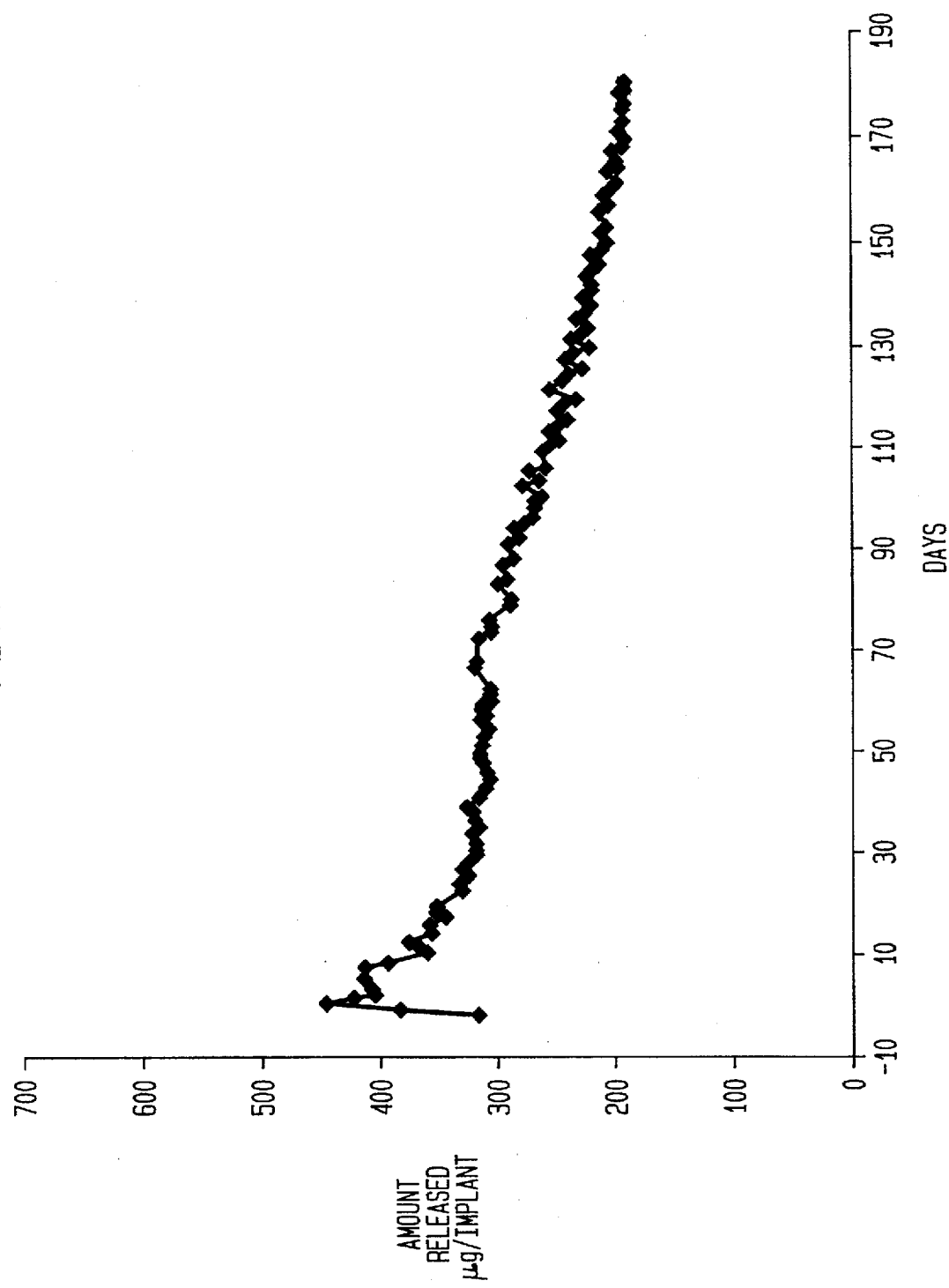
FIG. 5 is a graph showing the in vitro release profile of MENT Ac from implants made in accordance with the present invention over 180 days.

FIG. 5 illustrates the in vitro release profile of MENT Ac implants produced in accordance with Example 1 and tested as described in this example. The release profile can be characterized as somewhere between a first order release and a pseudo or near zero order release rate. Most importantly, however, acceptable pharmacological levels of MENT Ac were released throughout the entire 180 useful life of the implant.

Example 3

MENT Ac- Silastic® Implant(Comparison)
A. Preparation of SILASTIC® Core Including MENT Ac Equal parts of micronized MENT Ac and polydimethylsiloxane base (SILASTIC®), MDX4-4092 available from Dow-Corning were weighed out and mixed thoroughly to assure uniformity of drug distribution. Catalyst M (Stannous Octoate) was then added in proportions of approximately 0.4 g/8 g of the drug-polymer mixture. The mixture was again mixed, quickly but thoroughly.

The catalyzed drug-polymer mixture was then transferred to a stainless steel syringe and quickly injected into split transfer molds with cavities of 2.1–2.2 mm and 12 cm in length. A test sample of the mixture is set aside to be used to estimate when the material has hardened sufficiently. After the test sample of the mixture has hardened, the molds were opened and the core rods removed. The rods are then cut into desired lengths: For 4 cm rods, 4.0±0.2 cm; for 3 cm rods, 3.0±0.2 cm. Preferably, the rods are then weighed.
B. Coating The SILASTIC® Cores To Produce An Implant.

SILASTIC® Tubing (MDF0373), 0.080"×0.096" (ID× OD) is swollen in n-hexane and slipped over 50% (w/w) MENT Ac core rods prepared in Part A of Example 3. The SILASTIC® tubing extended beyond each end of the rod by about 0.5 cm.

The hexane was allowed to evaporate and the SILASTIC® tube to shrink firmly around the core rod. The protruding ends of the SILASTIC® tubing were then filled with Medical Grade Adhesive, Silicone Type A, available from Dow-Corning and allowed to cure. After curing, the ends of the implant were trimmed so that only about 2 mm of the cured adhesive remained at either end of the implant. The implants were then placed into Dual-Peel Self-Sealing Sterilization Pouch and sterilized with ethylene oxide.

Example 4

In Vitro Release Rate Estimate of MENT Ac From Silastic® Implants

A single SILASTIC® implant prepared in accordance with Example 3 was placed in a 20 ml capacity screw-capped glass vial. 20 ml of an incubation medium consisting of 1:750 aqueous solution of ZEPHIRAN® (benzalkonium chloride) was added and the vial was capped. The vial and content were placed into a shaker-water bath maintained at 37° C and shaken at a rate of 100 strokes/min (1 stroke=1 inch). The incubation medium was changed daily. Assay sample for MENT Ac content were measured by UV absorption spectrophotometry at 243 nm, using 1:750 aqueous solution of ZEPHIRAN® in the Reference Cell. Standards of MENT Ac in ZEPHIRAN® were prepared for comparison and assayed also at 243 nm. A standard curve was then constructed and the amount of MENT Ac in the sample determined. The release rate is expressed as µg MENT Ac/cm/day and plotted against the number of days of incubation; to give an in vitro release rate profile.

Figure 2:
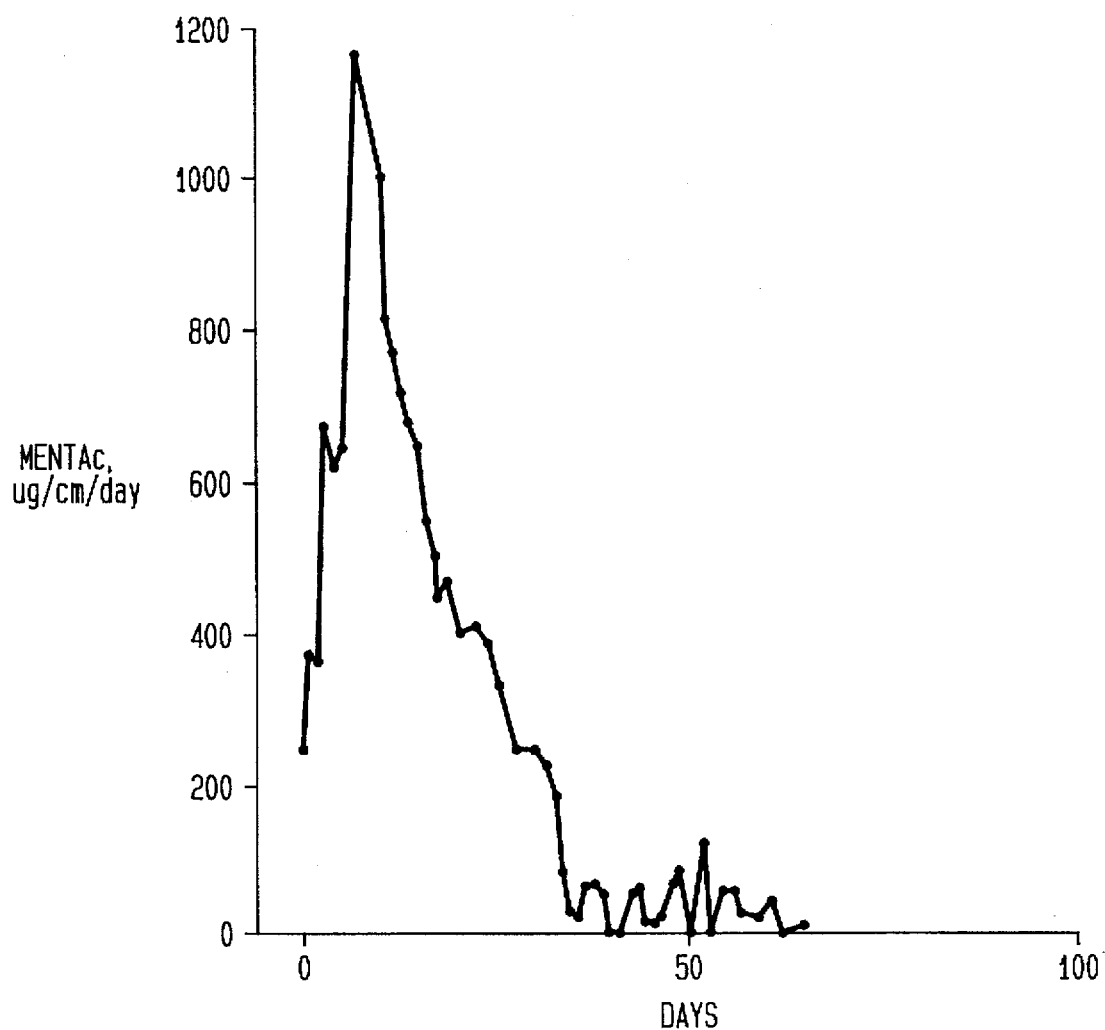
FIG. 2 is a graph showing the in vitro release rate of MENT Ac from 50% MENT Ac silicone elastomer rods covered with silicone elastomer tubing.
Figure 3:
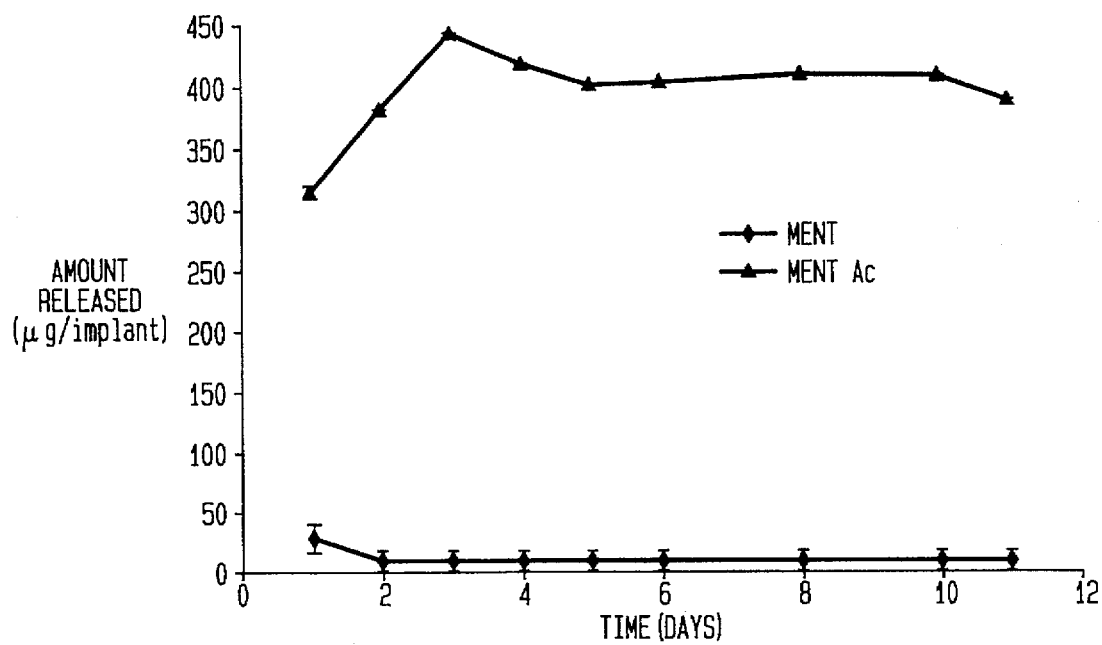
FIG. 3 is a graph showing the in vitro release profile of MENT AND MENT Ac from EVA implants.

The in vitro release rate profile is shown in FIG. 2. The rate of release of MENT Ac is extremely high and near zero-order release rate profile of the steroid is not achieved. The effective life-span of the implant is less than 50 days.

We claim:

1. An implantable system, comprising: a first implant intended for subcutaneous or local administration of an androgen, said first implant including an androgen in an amount which is sufficient to provide the daily dose of a pharmaceutically effective amount of said androgen over a predetermined time dispersed in a core formed of a first ethylene vinyl acetate copolymer, and a membrane encasing said core and said androgen, said membrane formed of a second ethylene vinyl acetate copolymer; and a second implant intended for subcutaneous or local administration of a sterilitant, said second implant including said sterilitant in an amount sufficient to provide for the daily dose of a pharmaceutically effective amount of said sterilitant over said predetermined time.

2. The implantable system of claim 1, wherein said first implant and said second implant are of a cooperative size and shape and are designed such that each releases a pharmaceutically complementary amount of said androgen and said sterilitant; so as to provide treatment to a patient in need thereof.

3. The implantable system of claim 1, wherein said first ethylene vinyl acetate copolymer of said first implant has a molecular weight such that the melt index is greater than 10 grams/10 minutes, and a vinyl acetate content of at least 20% by weight.

4. The implantable system of claim 3, wherein said first ethylene vinyl acetate copolymer of said first implant comprises an ethylene vinyl acetate copolymer with a melt index between 25 and 30 grams/10 minutes and a vinyl acetate content of at least 25% by weight.

5. The implantable system of claim 1, wherein said second ethylene vinyl acetate copolymer of said first implant has a molecular weight such that the melt index is less than 10 grams/10 minutes, and a vinyl acetate content of less than 20% by weight.

6. The implant of claim 5 wherein said second ethylene vinyl acetate copolymer of said first implant comprises ethylene vinyl acetate copolymer with a melt index of 8 grams/10 minutes or less, and a vinyl acetate content of less than 20% by weight.

7. The implantable system of claim 1, wherein said androgen is selected from the group consisting of MENT, MENT Ac, testosterone, methandroil, oxymetholone, methandienone, oxymesterone, nondrolone phenylpropionate, norethandrolone and pharmaceutically acceptable esters thereof.

8. The implantable system of claim 7, wherein said androgen is MENT.

9. The implantable system of claim 7, wherein said androgen is MENT Ac.

10. The implantable system of claim 1, wherein said pharmaceutically effective amount of said androgen is provided in an amount which is sufficient to provide for the required daily dose of a pharmaceutically effective amount of said androgen over a predetermined time of at least about 7 days.

11. The implantable system of claim 1, wherein said predetermined time is at least about 100 days.

12. The implantable system of claim 11, wherein said predetermined time is at least about 180 days.

13. The implantable system of claim 1, wherein said androgen is provided in an amount which is sufficient to provide a daily dose of between about 100 and about 1000 micrograms of androgen per day.

14. The implantable system of claim 13, wherein said androgen is provided in an amount which is sufficient to provide a daily dose of between about 300 and about 500 micrograms of androgen per day.

15. The implantable system of claim 1, wherein said core of said first implant consists of from about 50 to about 75% androgen and from about 50 to about 25% of said ethylene vinyl acetate copolymer.

16. The implantable system of claim 1, wherein said second implant includes a biocompatible, non-biodegradable, water-swellable, water-insoluble, hydrophilic cartridge of a copolymer AB having from about 25 to about 70 weight percent of monomer A which are 2-hydroxy ethyl methacrylate units and from about 75 to about 30 weight percent of monomer B units and possessing a predetermined EWC value in the range of from about 25 to about 75 weight percent;

a sealant for closure of an open-end of said cartridge comprising a plug of biocompatible, non-biodegradable, water-swellable, water-insoluble, hydrophilic polymer having an equilibrium water content value greater than that of the cartridge;

with said sterilitant contained in a reservoir disposed within said cartridge.

17. The implantable system of claim 16, wherein said monomer B includes hydroxypropyl methacrylate units.

18. The implantable system of claim 16, wherein said sterilitant is provided in an amount of between about 5 mg and about 50 mg.

19. The implantable system of claim 1, wherein said sterilitant is LHRH or an LHRH analog.

20. The implantable system of claim 19, wherein said sterilitant is LHRH or an LHRH analog.

21. An implant intended for subcutaneous or local administration comprising:

androgen in an amount sufficient to provide for the required daily dose of a pharmaceutically effective amount of said androgen over a predetermined time;

a core of ethylene vinyl acetate copolymer having a sufficient molecular weight so as to result in a melt index which is greater than 10 grams/10 minutes, and a vinyl acetate content of at least about 20% by weight, said core material incorporating said androgen; and a membrane encasing said core and said androgen and said membrane including ethylene vinyl acetate having a molecular weight which results in a melt index which is less than 10 grams/10 minutes and a vinyl acetate content of less than 20% by weight.

22. The implant of claim 21, wherein said androgen is selected from the group consisting of MENT, MENT Ac, testosterone; esters of testosterone, methandroil, oxymetholone, methandienone, oxymesterone, nondrolone phenylpropionate and norethandrolone.

23. The implant of claim 22, wherein said androgen is MENT.

24. The implant of claim 22, wherein said androgen is MENT Ac.

25. The implant of claim 21, wherein said pharmaceutically effective amount of said androgen is provided in an amount sufficient to provide for the required daily dose of a pharmaceutically effective amount of said androgen over a predetermined time of at least 7 days.

26. The implant of claim 25, wherein said predetermined time is at least about 100 days.

27. The implant of claim 26, wherein said predetermined time is at least about 180 days.

28. The implant of claim 21, wherein said androgen is provided in an amount sufficient to provide a daily dose of between about 100 and about 1000 micrograms of androgen per day.

29. The implant of claim 28 wherein said androgen is provided in an amount sufficient to provide a daily dose of between about 300 and about 500 micrograms of androgen per day.

30. The implant of claim 21 wherein said core consists of from about 50 to about 75% androgen and from about 50 to about 25% of said ethylene vinyl acetate copolymer.

31. The implant of claim 21, wherein the core material comprises an ethylene vinyl acetate copolymer with a melt index between 25 and 30 grams/10 minutes and a vinyl acetate content of greater than 20% by weight.

32. The implant of claim 21 wherein the membrane comprises ethylene vinyl acetate copolymer with a melt index of 8 grams/10 minutes or less, and a vinyl acetate content of less than 20% by weight.

33. A pharmaceutical kit comprising: a first implant intended for subcutaneous or local administration of an androgen, a second implant intended for a subcutaneous or local administration of a sterilitant, said first implant and said second implant having a cooperative size and shape and being designed such that each release a pharmaceutically complementary amount of said androgen and said sterilitant to a patient in need of treatment, said first implant and said second implant being loaded in a delivery means for a subcutaneous implantation of said implants.

34. The kit of claim 33 wherein said first implant includes:

androgen in an amount sufficient to provide for the required daily dose of a pharmaceutically effective amount of said androgen over a predetermined period;

a core of ethylene vinyl acetate copolymer having a sufficient molecular weight so as to result in a melt index which is greater than 10 grams/10 minutes, and a vinyl acetate content of at least about 20% by weight, said core material incorporating said androgen; and a membrane encasing said core and said androgen and said membrane including ethylene vinyl acetate having a molecular weight which results in a melt index which is less than 10 grams/10 minutes and a vinyl acetate content of less than 20% by weight.

35. The kit of claim 34 wherein said second implant includes said sterilitant in an amount sufficient to provide for the daily dose of a pharmaceutically effective amount of said sterilitant over said predetermined time.

36. The kit of claim 33 wherein said delivery means is selected from the group consisting of syringes and trocars.

* * * * *

UNITED STATES PATENT AND TRADEMARK OFFICE
CERTIFICATE OF CORRECTION

PATENT NO. : 5,733,565
DATED : March 31, 1998
INVENTOR(S) : Moo-Young, et al

It is certified that error appears in the above-indentified patent and that said Letters Patent is hereby corrected as shown below:

Column 9, line 55, "("HEM")" should read --("HEMA")--.

Column 9, line 55, "("HPFLA")" should read --("HPMA")--.

Column 12, line 49, "Eva" should read --EVA--.

Signed and Sealed this

Twenty-third Day of June, 1998

Attest:

BRUCE LEHMAN

*Attesting Officer*     *Commissioner of Patents and Trademarks*